United States Patent [19]

Farr et al.

[11] Patent Number: 5,521,144

[45] Date of Patent: May 28, 1996

[54] HERBICIDE COMPOSITION

[75] Inventors: Jennifer Farr, Elkhart; Phillip K. Lee, Fort Wayne, both of Ind.

[73] Assignee: Central Soya Company, Inc., Fort Wayne, Ind.

[21] Appl. No.: 229,999

[22] Filed: Apr. 19, 1994

Related U.S. Application Data

[63] Continuation of Ser. No. 947,343, Sep. 18, 1992, abandoned.

[51] Int. Cl.$^6$ .......................... A01N 47/36; A01N 43/66
[52] U.S. Cl. .......................... 504/215; 504/214; 504/230; 504/231; 71/DIG. 1
[58] Field of Search .......................... 71/DIG. 1; 504/116, 504/214, 215, 230, 231

[56] References Cited

U.S. PATENT DOCUMENTS

| | | | |
|---|---|---|---|
| 2,296,933 | 9/1942 | Jordan | 252/316 |
| 2,626,862 | 1/1953 | Zimmerman et al. | 71/113 |
| 2,849,318 | 8/1958 | Julian et al. | 99/15 |
| 3,069,361 | 12/1962 | Cogswell | 252/363.5 |
| 3,645,716 | 2/1972 | Rutkowski | 71/113 |
| 3,709,676 | 1/1973 | Vartiak | 71/92 |
| 3,900,421 | 8/1975 | Fusey | 252/312 |
| 3,948,635 | 4/1976 | Vachette et al. | 71/92 |
| 4,125,400 | 11/1978 | Downer et al. | 71/127 |
| 4,133,674 | 1/1979 | Cartwright et al. | 71/93 |
| 4,200,551 | 4/1980 | Orthoefer | 252/312 |
| 4,252,793 | 2/1981 | Altman | 424/199 |
| 4,557,751 | 12/1985 | Ronning et al. | 71/91 |
| 4,626,274 | 12/1986 | Hausmann et al. | 71/93 |
| 4,666,747 | 5/1987 | Quinn | 427/421 |
| 4,678,710 | 7/1987 | Sakimoto et al. | 428/407 |
| 4,840,942 | 6/1989 | Iwasaki et al. | 514/120 |
| 4,931,089 | 6/1990 | Martin | 71/121 |
| 4,975,110 | 12/1990 | Puritch et al. | 71/113 |
| 5,004,493 | 4/1991 | Norris | 71/DIG. 1 |
| 5,035,741 | 7/1991 | Puritch et al. | 71/113 |
| 5,041,156 | 8/1991 | Suchy et al. | 71/92 |
| 5,143,539 | 9/1992 | Lovell | 71/92 |
| 5,201,936 | 4/1993 | Betram et al. | 504/289 |
| 5,260,260 | 10/1993 | Gednalske et al. | 504/206 |

OTHER PUBLICATIONS

Yasuo Ogawa et al, Herbicidal Method Using Sulfonamides, Surfactants and Oils of Hydrocarbons, 5–Agrochemicals, vol. 111, 1987, 189595X.

Kimura et al, SL–950, A Novel Sulfonylarea Herbicide for Corn, 5–Agrochemicals, vol. 112, 1990, 173972C.

Donald Frear, Chemistry of Insecticides and Fungicides, 1943, pp. 123–130 & 184–185.

Merck Index, 9th Edition, p. 327, 1976.

*Primary Examiner*—Richard L. Raymond
*Assistant Examiner*—Deborah Lambkin
*Attorney, Agent, or Firm*—Baker & Daniels

[57] ABSTRACT

An adjuvant composition for use in a pesticide formulation that is applied to a substrate. The adjuvant composition comprises acidulated soap stock. A surfactant and/or mixed tocopherols may be added to the adjuvant.

14 Claims, No Drawings

HERBICIDE COMPOSITION

This is a continuation of application Ser. No. 07/947,343, filed on Sep. 18, 1992, now abandoned.

BACKGROUND OF THE INVENTION

This invention relates to adjuvants for use in a pesticide formulation, and in particular to an environmentally compatible adjuvant composition prepared from acidulated soap stock.

It has long been common for farmers, homeowners, etc., to utilize pesticides to control the undesired proliferation of weeds, insects, rodents, and the like. Among the pesticides most commonly encountered are herbicides, which are used to destroy or inhibit undesired plant growth, and insecticides, which are used to destroy or repel insects.

As a result of efforts to clean up the environment, and in furtherance of ongoing efforts to minimize the future introduction of environmental contaminants into the soil, air and water, the use of pesticides has come under increased scrutiny in recent years. Numerous efforts have been made to reduce the toxicity and other harmful effects of pesticides on the environment, and at the same time to maintain or even improve the efficacy of the pesticides.

An adjuvant is a substance that is present in a pesticide formulation, or added to a pesticide formulation, to increase the efficacy of the pesticide or to improve the application characteristics of the pesticide. At the present time, adjuvants are typically made from petroleum based oils. Adjuvants are presently in widespread use in agriculture to increase the efficacy of various pesticides, including post-emergent herbicides. Post-emergent herbicides are herbicides that are applied after the germination of the crops and their appearance above the ground, and generally after the appearance of unwanted vegetation.

When used with post-emergent herbicides, adjuvants may act in many different ways to improve the efficacy of the herbicide. For example, adjuvants have commonly been used to improve the "wetting" of drops during spraying, to alter the volatility of the spray mixture, to improve the rain-fastness of the herbicide on the plant, to improve the penetration of the herbicide active ingredient (AI) into the target plant, to regulate the pH of the spray mix, to improve the distribution of the AI over the plant, to improve the compatibility of various crop protection agents in the mix tank and to reduce drift during spraying. Each of the beneficial characteristics of adjuvants acts in some manner to improve the effectiveness of the herbicide. As a result, the amount of herbicide that is applied for crop protection may be reduced in many cases, without a concomitant loss in efficacy of the herbicide.

Several general classifications of adjuvant materials in use with herbicides are known. As stated in a report by Colin A. Houston & Associates, Inc., titled, "Industrial Applications of Surfactants, North American Forecast to 1995" March 1987, which report is incorporated herein by reference, these classifications include activator adjuvants, spray modifier adjuvants, and utility modifier adjuvants. The classifications are further described below.

Activator adjuvants function to increase the apparent biological activity of the herbicides beyond the activity of that obtained by the herbicide alone. Within this classification are surfactants, crop oils, and crop oil concentrates. Surfactants improve the emulsifying, dispersing, spreading, and/or wetting characteristics of the spray mixture. Crop oils are nonphytotoxic mineral or vegetable oils which contain 1–2% surfactants and function in a manner similar to surfactants. Crop oil concentrates consist of mineral or vegetable oils with 17–20% added surfactant. These materials aid in penetration through the plant cuticle, and in reducing the surface tension of the spray droplets (wetting ability).

Spray modifier adjuvants modify the spray solution in a specified manner. This modification occurs either in the tank, in transit to the target, or in the target itself. Spray modifier adjuvants include spreaders, stickers, spreader-stickers, foaming agents, and thickeners. Spreaders function to increase the area of the spray droplets on the target substrate. Stickers function to adhere the spray droplets to the target surface, and increase the rain-fastness of the droplets. Spreader-stickers combine the functions of spreaders and stickers as described above. Foaming agents increase the surface area of air-filled liquid spray droplets. Thickeners function to increase the viscosity of the spray mixture, and to reduce the spray drift.

Utility modifier adjuvants function to broaden the range of conditions under which a given herbicide formulation may be used for maximum results. Specific utility modifier adjuvants include anti-foam agents, compatibility agents, and buffering agents. Anti-foam agents decrease and/or prevent foaming when the solution containing the herbicide formulation is agitated or sprayed. Compatibility agents function to allow and maintain an emulsification of two or more ingredients that would otherwise separate when mixed. Buffering agents function to moderate the pH of the water in the tank solution.

Agricultural adjuvants that are used with post-emergent herbicides are generally a blend of compounds comprising a surfactant (usually nonionic), as well as other active and inert ingredients. These adjuvants are commonly manufactured from petroleum-based oils and surfactants. The current trend toward more environmentally responsible agricultural chemicals creates a need for adjuvant products that are less harmful to the environment than prior art adjuvants, and that will allow greater herbicide efficacy at lower dosage rates.

Due to the aforementioned environmental concerns, as well the ever-present desire to provide the most effective product at the least overall cost, certain shortcomings have persisted in the art arising from the use of existing adjuvants in combination with conventional herbicides. For example, the prior art adjuvants do not provide the degree of penetration into the target substrate that is desired. A greater penetration into the substrate provides for greater efficacy, and thus allows the use of a smaller dosage of herbicide in order to obtain comparable visual injury to the substrate when compared to that obtained with larger doses of conventional adjuvants.

In addition, the targeted plant's metabolic defenses are often able to provide some degree of protection to the plant from the herbicide's active ingredient, thus limiting the efficacy of the herbicide. Due to the action of the plant's metabolic defenses against the herbicide, it is generally necessary to use a larger dose of the pesticide active ingredient than would be necessary if the metabolic defenses were not able to provide this protection to the plant.

It is desired to provide an adjuvant composition that enhances the efficacy of the pesticide. It is similarly desired to provide an adjuvant composition that allows greater penetration of the media into the target substrate. It is further desired to improve the protection of the herbicide's active ingredient against the plant's metabolic defenses by providing an adjuvant composition that allows more of the herbicide's active ingredient to reach the targeted areas of the substrate. Additionally, it is desired to provide an adjuvant composition that is less harmful to the environment than prior art adjuvants, and that enables a reduction to be made in the amount of the active ingredient that is applied to the substrate, and thus released into the environment.

SUMMARY OF THE INVENTION

The present invention, in one form thereof, provides an adjuvant composition for use with pesticides which addresses the concerns expressed above. The inventive adjuvant composition comprises acidulated soap stock and, preferably, a surfactant. Mixed tocopherols may be added to the adjuvant composition. The inventive composition allows greater penetration of the media into the target substrate than was obtained with prior art compositions. Additionally, the use of the inventive adjuvant allows more of the herbicide's active ingredient to reach the targeted areas of the substrate. Further, the use of the present adjuvant composition enables one to reduce the amount of the pesticide's active ingredient that is applied onto the substrate, and thus introduced into the environment.

The present invention further provides, in one form thereof, a herbicidal composition comprising as a major constituent a herbicidally-active agent, and including an effective amount of acidulated soap stock to increase the efficacy of the herbicidally-active agent.

DETAILED DESCRIPTION OF THE INVENTION

The present invention comprises an adjuvant composition for use with pesticides that is made from acidulated soap stock. It is well known that many plant species contain oils, which oils may be extracted from the plant and beneficially utilized for various purposes. Soap stock is a by-product of alkali refining of crude vegetable, or animal, fats and oils. The refining process is performed to remove the free fatty acids; that is, the fatty acids that have disassociated from a triglyceride. Sodium hydroxide is mixed with the crude oil and allowed to react. This forms sodium salts of the free fatty acids, which salts ("soap stock") precipitate out as a solid and are removed from the oil. Oils containing free fatty acids that may be readily refined into soap stock may be extracted from many different plants. A major source of these oils is soybeans. Other sources are canola, corn, cottonseed and olives, and to a lesser degree, sunflower, safflower, sesame, peanut, rapeseed, rice, various tropical oils, and other vegetable derived oils.

Soap stock is acidulated in vegetable oil refineries with sulfuric acid or other suitable strong acids to form acidulated soap stock, otherwise known as "acid oil". Soap stock is a viscous material with a high amount of solids. The acidulation process disassociates the fatty acid salts, thus removing the solids and forming a fluid that is much easier to handle. Although strong acids, such as hydrochloric acid, nitric acid, phosphoric acid, and the like, may be utilized in the acidulation, sulfuric acid is generally the acid of choice, primarily for cost reasons. Soap stock and acid oil are also used as sources of fatty acid by companies that distill and purify them. Acid oil is a liquid having a pH range between 2 and 4. Acid oil also contains small amounts of a complex mixture of minerals, such as sodium, sulphur, and phosphorous. Typically, acid oil has been a waste product obtained during alkali refining, and has often been discarded. At the present time, the major use that is made of acid oil is in soap manufacturing or as an additive to domestic animal feed.

The inventive adjuvant composition for use with pesticides comprises acidulated soap stock and, optionally, a surfactant. The adjuvant composition is intended for use with pesticides to improve the efficacy of the pesticide. In particular, the inventive composition is intended for use with common herbicides, particularly post-emergent herbicides.

It is well known by those skilled in the art that herbicides are typically classified by chemical family, mode of action, mode of application (i.e. soil applied or sprayed, pre- or post-emergent) or typical usage (i.e. type of crop, target weeds, etc.). Generally, adjuvants are used with spray-applied post-emergent herbicides. The inventive adjuvant composition is particularly useful with sulfonyl urea herbicides, such as nicosulfuron, primisulfuron and thifensulfuron, however those skilled in the art will recognize that beneficial results may similarly be obtained with a variety of other known herbicides.

Without the use of adjuvant compositions, herbicides alone are often ineffective in causing injury to the weed or other objectionable plant material to be eradicated. For example, the rain-fastness of a herbicide may be such that the herbicide will be washed from the weed before the beneficial action of the active ingredient has occurred. Similarly, the surface tension of the aqueous droplets of the herbicide may prevent the herbicide from covering a wide area of the substrate, thus minimizing the surface area available for the entry of the herbicide into the substrate and reducing the effective activity of the herbicide.

A wide variety of post-emergent herbicides that are currently in use were tested on corn and soybeans. In all cases, an increase in herbicide efficacy was observed when using the test adjuvant as compared to the herbicide alone. Although performance did not exceed industry standards in all cases, exceptional performance was noted when the test adjuvant composition was used with sulfonyl urea herbicides such as nicosulfuron, primisulfuron and thifensulfuron, and comparable performance with a variety of other herbicide families. Even in those instances when industry standards were not exceeded, the acid oil adjuvant provides environmental benefits when compared to conventional petroleum-based adjuvants.

Although it is not necessary to include a surfactant with the acidulated soap stock ("acid oil") adjuvant in order to obtain beneficial results, optimum results may be obtained in most cases with the addition of a surfactant. Preferred surfactants include nonionic surfactants, such as alkylphenol ethoxylates (APE) or blends of alcohol ethoxylates and glycol ethers, and anionic surfactants, such as organo phosphate esters, or a blend of nonionic and anionic surfactants. Examples of specific surfactants that can be utilized for beneficial results include alkylbenzene sulfonates, alcohol ethoxylates, alkylphenol ethoxylates, ethoxylated sorbitan esters, polyethylene glycol esters, sorbitan esters, sulfosuccinates, phosphate esters, ethoxylated tallow amines and blends of the above surfactants. Examples of additional surfactants that may also be acceptable for specific applications are well known to those of ordinary skill in the art.

In some cases it was found that the use of anionic surfactants provided superior performance when compared to nonionic surfactants, however the use of nonionic surfactants is preferred because of the combination of performance characteristics and the generally lower cost of nonionic surfactants, particularly when compared to phosphate esters stock contains naturally occurring tocopherols.

Soap stock contains naturally occurring tocopherols. Tocopherols are referred to as any of several closely related substances having vitamin E activity that occur naturally in certain oils, such as soap stock. Typically, tocopherols are naturally present in acid oil in amounts that generally range between about 0.08% and 0.20%. Although the exact action of tocopherols is not fully known, it has been discovered that the presence of tocopherols in the soap stock also enhances the beneficial action of the adjuvant in many cases. It is believed that tocopherols act as anti-oxidants that protect the herbicide from being oxidized and/or metabolized by the target substrate, and thereby rendered non-functional.

In addition to the naturally occurring tocopherols described above, it has been determined that the addition of a controlled amount of additional mixed tocopherols to the acid oil further enhances the beneficial activity of the adjuvant. Mixed tocopherols may be obtained as a by-product of deodorization of fats and oils, and are commercially available, for example, from Eastman or Henkel. Examples 3 and 4 below illustrate the improvement that may be noted in the visual injury to johnsongrass and giant foxtail when mixed tocopherols are added to a pesticide composition including the test adjuvant.

The following non-limiting examples serve to further illustrate the invention.

EXAMPLE 1

A test adjuvant composition comprising a 4:1 mixture of acid oil (AO) and a surfactant (APE) was tank mixed at levels of from 0.0% to 2.0% with either nicosulfuron or primisulfuron herbicides. The alkylphenol ethoxylate surfactant utilized in the tests is commercially available from Harcross Chemicals, Inc. The resulting pesticide composition was applied to johnsongrass (*Sorghum halepense*) and giant foxtail (*Setaria faberii*). The nicosulfuron was applied at a rate of 1.5 gm ai/A. The primisulfuron was applied at a rate of 6.0 gm ai/A on johnsongrass and 0.8 gm ai/A on giant foxtail. The tank mixture was applied at a rate of 25 gal/A.

The johnsongrass and giant foxtail plants were grown in a greenhouse to the 3–4 leaf stage prior to spraying. The plants were rated for visual injury 14 days after treatment (DAT). Visual injury is scored on a scale of 0 to 100, with 0 indicating a healthy plant sustaining no damage, and 100 indicating death.

The results of the test are presented in Table 1.

TABLE 1

| | % Visual Injury (14 DAT) | | | |
| --- | --- | --- | --- | --- |
| | Nicosulfuron | | Primisulfuron | |
| Level | JG | GF | JG | GF |
| 0.0 | 0 | 0 | 0 | 0 |
| 0.2 | 19 | 40 | 23 | 41 |
| 0.4 | 24 | 41 | 26 | 56 |
| 0.6 | 51 | 66 | 61 | 70 |
| 0.8 | 63 | 80 | 68 | 81 |
| 1.0 | 73 | 93 | 69 | 93 |
| 1.2 | 74 | 91 | 70 | 91 |
| 1.4 | 75 | 91 | 68 | 91 |
| 1.6 | 74 | 90 | 65 | 91 |
| 1.8 | 71 | 91 | 70 | 88 |
| 2.0 | 75 | 88 | 70 | 84 |

As shown in Table 1, no visual injury to the substrate was observed after 14 days with the test samples having no added adjuvant, i.e. the 0.0% level of added adjuvant. The beneficial effect of the adjuvant may also be observed to decrease at about a 2.0% inclusion rate.

EXAMPLE 2

The preferred acid oil to surfactant ratio ranges from about 9:1 to about 3:7, with about 8:2 (4:1) being most preferred. The following example illustrates the visual injury observed at the following ratios of AO:APE. A series of test adjuvants were made using acid oil:surfactant ratios ranging from 10:0 to 0:10. The adjuvants were each tank mixed at a 1% level with either nicosulfuron or primsulfuron and applied to johnsongrass and giant foxtail. The nicosulfuron was applied at a rate of 1.5 gm ai/A. The primisulfuron was applied at a rate of 6.0 gm ai/A on johnsongrass and 0.8 gm ai/A on giant foxtail. The tank mixture was applied at a rate of 25 gal/A.

The johnsongrass and giant foxtail plants were grown in a greenhouse to the 3–4 leaf stage prior to spraying. The plants were rated for visual injury 14 days after treatment (DAT).

TABLE 2

| | % Visual Injury (14 DAT) | | | |
| --- | --- | --- | --- | --- |
| | Nicosulfuron | | Primisulfuron | |
| AO:APE | JG | GF | JG | GF |
| 10:0 | 45 | 35 | 6 | 14 |
| 9:1 | 70 | 80 | 70 | 84 |
| 8:2 | 74 | 89 | 75 | 91 |
| 7:3 | 73 | 88 | 74 | 90 |
| 6:4 | 71 | 90 | 71 | 86 |
| 5:5 | 70 | 86 | 69 | 89 |
| 4:6 | 68 | 86 | 68 | 85 |
| 3:7 | 69 | 88 | 68 | 86 |
| 2:8 | 66 | 83 | 66 | 83 |
| 1:9 | 68 | 76 | 64 | 81 |
| 0:10 | 65 | 81 | 61 | 78 |

Although beneficial results may be obtained with the use of either the adjuvant composition without surfactant, or alternatively, surfactant without the adjuvant composition, optimum results are obtained with an 8:2 (4:1) mix of AO:APE. If the surfactant is present in the adjuvant composition in a ratio greater than about 3:7, it was noticed that crop damage begins to occur.

EXAMPLE 3

Mixed tocopherols from soy distillate were added to a test adjuvant composition as described in Example 1 comprising a 4:1 mixture of acid oil:APE. The adjuvants were mixed at a 1% level with nicosulfuron, used at a rate of 1.5 gm ai/A and applied to seedling johnsongrass (grown to the 3–4 leaf stage in a greenhouse) at a spray volume of 25 gal/A. The results are shown in Table 3:

TABLE 3

| Treatment | Level of Added Mixed Tocopherols (%) | Visual Injury (%) to Johnsongrass 14 DAT |
| --- | --- | --- |
| Untreated Control | — | 0 |
| Nicosulfuron + | 0.0 | 79 |
| Test Adjuvant + | 0.2 | 84 |
| | 0.4 | 93 |
| | 0.6 | 90 |
| | 0.8 | 90 |
| | 1.0 | 90 |

TABLE 3-continued

| Treatment | Level of Added Mixed Tocopherols (%) | Visual Injury (%) to Johnsongrass 14 DAT |
|---|---|---|
| | 2.0 | 86 |
| | 4.0 | 85 |
| | 8.0 | 60 |

An increase in herbicide efficacy was observed when compared to the composition without the added mixed tocopherols. The beneficial effect of the added tocopherols continues to be observed at a 4% level, although it is not as pronounced as at lower levels. The beneficial effect disappears totally at the 8% level, and in fact the addition of tocopherols has a deleterious effect. This is believed to be due to a shift in the equilibrium of the reaction to an extent that the tocopherols begin to act as a pro-oxidant, rather than an anti-oxidant, at this level.

EXAMPLE 4

When the test adjuvant containing added mixed tocopherols (from soy distillate) is applied to giant foxtail with primisulfuron, an increase in herbicide efficacy is also observed, when compared to the formula without the added tocopherols. The above adjuvant mixtures were mixed at a 1% level with primisulfuron, used at a rate of 1.5 gm ai/A and applied to giant foxtail (grown to the 3–4 leaf stage in a greenhouse) at a spray volume of 25 gal/A. The results are shown in Table 4:

TABLE 4

| Treatment | Level of Added Mixed Tocopherols (%) | Visual Injury (%) to Giant Foxtail 14 DAT |
|---|---|---|
| Untreated Control | — | 0 |
| Primisufuron + | 0.0 | 65 |
| Test Adjuvant + | 0.2 | 70 |
| | 0.4 | 74 |
| | 0.6 | 73 |
| | 0.8 | 70 |
| | 1.0 | 69 |
| | 2.0 | 66 |
| | 4.0 | 63 |
| | 8.0 | 46 |

The results are similar to those of Example 3. Once again, an increase in herbicide efficacy was observed when compared to the composition without the added mixed tocopherols. Also, the beneficial effect of the tocopherols levels off around the 2–4% level of added tocopherol. Once again the addition of tocopherols at the 8% level is shown to actually be deletious to the pesticide composition, and the visual injury to the targeted substrate is reduced below that observed at the 0.0% tocopherol level.

The following examples illustrate the effects of a test adjuvant mixture of acid oil:APE (4:11) compared to presently commercially available adjuvants.

EXAMPLE 5

An adjuvant mixture of acid oil:APE (4:1) was mixed at a 1% level with $C^{14}$ labeled nicosulfuron at a rate of 14 grams active ingredient/acre (gm ai/A), and applied to seedling johnsongrass and giant foxtail as a 2 µl spot (containing a radioactivity level of 0.01 µCi) to the adaxial surface of the plant leaf. The grass plants had been grown in a greenhouse to the 3–4 leaf stage prior to the test. After 0, 6 and 24 hour periods, the treated leaves were rinsed for 45 seconds with 100% methanol. The results were radioassayed by scintillation spectrophotometry to calculate the percent of the labeled herbicide absorbed (i.e. not washed off). The commercially available adjuvant X-77 (Chevron), was used at the manufacturer's suggested optimal rate of 0.5%, and commercially available adjuvant SCOIL (Agsco) was used at a rate of 1% for comparison. In this study there were a minimum of four replications and the study was performed twice. The results are shown in Table 5:

TABLE 5

| | C14 Nicosulfuron Absorption (%) | | | | | |
|---|---|---|---|---|---|---|
| | Seedling Johnsongrass | | | Giant Foxtail | | |
| Treatment | 0 hrs | 6 hrs | 24 hrs | 0 hrs | 6 hrs | 24 hrs |
| No adjuvant | —* | — | — | 2.0 | 6.3 | 6.2 |
| Test adjuvant | 2.0 | 15.4 | 63.1 | 1.7 | 48.1 | 86.4 |
| X-77 | 1.9 | 15.1 | 20.0 | 3.3 | 18.6 | 25.8 |
| SCOIL | 0.7 | 17.5 | 38.6 | 1.4 | 27.1 | 50.5 |

*The 2 µl drop of the herbicide solution without the adjuvant would roll off the leaf, so evaluation was not possible.

EXAMPLE 6

The adjuvant mixture of Example 5 was tank mixed at a 1% level with nicosulfuron at a rate of 3.5 gm ai/A and 7 gm ai/A, and applied to plots of field corn for control of annual grasses at a rate of 25 gal/A. Plots treated with the identical herbicide concentration and rate as above (without test adjuvant), but using a 1% inclusion rate of Crop Oil Concentrate (COC) were tested for comparison. The particular COC utilized in the testing was Herbimax, available from Loveland Industries. COC is a widely-used adjuvant in agriculture, and typically comprises about 83% vegetable or petroleum oil and 17% nonionic surfactant. The plots were analyzed for percent control by comparing the weed populations of the experimental plots to the untreated control. The results are shown in in Table 6:

TABLE 6

| | Nicosulfuron Dose | | | | | |
|---|---|---|---|---|---|---|
| | 3.5 gm ai/A | | | 7 gm ai/A | | |
| | DAT | | | | | |
| | 10 | 32 | 62 | 10 | 32 | 62 |
| Treatment | Control Percentage | | | | | |
| Test Adjuvant | 75.7 | 73.3 | 70.0 | 83.7 | 89.3 | 89.3 |
| COC | 68.3 | 31.7 | 25.0 | 72.7 | 53.3 | 48.3 |
| Untreated Control | 0.0 | 0.0 | 0.0 | 0.0 | 0.0 | 0.0 |

It is observed that the control of the weed population in the samples with the COC decreases with the increase in number of days after treatment. This indicates that the functionality of the COC wears out with time. This effect is only minimally noted with the test adjuvant.

EXAMPLE 7

When the test adjuvant described in Example 1 is applied to quackgrass (*Agropyron repens*) with a mixture of nicosulfuron and thifensulfuron an increase in herbicide efficacy is observed when compared to the commercially available adjuvant X-77 (Chevron). The above adjuvant mixture was mixed at a 1% level with nicosulfuron, used at a rate of 6 gm ai/A and thifensulfuron, added at 5:1 ratio rate with nicosulfuron. The mixture was applied at a spray volume of 25 gal/A to quackgrass grown in a greenhouse. The X-77 was mixed at a 0.5% level with the above herbicide mixture as well as with each herbicide alone. The plants were rated after 14 days for visual injury. The results are shown in Table 7:

TABLE 7

| Treatment | Visual Injury (%) to Quackgrass 14 DAT |
|---|---|
| Untreated Control | 0 |
| Nicosulfuron + X-77 | 63 |
| Thifensulfuron + X-77 | 0 |
| Nicosulfuron/Thifensulfuron | |
| + X-77 | 62 |
| + Test Adjuvant | 89 |

EXAMPLE 8

When the test adjuvant described in Example 1 is applied to quackgrass with a mixture of primisulfuron and thifensulfuron an increase in herbicide efficacy is observed when compared to X-77 (Chevron). The above adjuvant mixture was tank mixed at a 1% level with primisulfuron, used at a rate of 6 gm ai/A and thifensulfuron, added at a 5:1 ratio rate with primisulfuron. The mixture was applied to quackgrass grown in a greenhouse at a spray volume of 25 gal/A. The X-77 was mixed at a 0.5% level with the above herbicide mixture as well as with each herbicide alone. The results are shown in Table 8:

TABLE 8

| Treatment | Visual Injury (%) to Quackgrass 14 DAT |
|---|---|
| Untreated Control | 0 |
| Primisulfuron + X-77 | 56 |
| Thifensulfuron + X-77 | 0 |
| Primisulfuron/Thifensulfuron | |
| + X-77 | 55 |
| + Test Adjuvant | 66 |

EXAMPLE 9

When the test adjuvant is applied to seedling johnsongrass and giant foxtail with a mixture of nicosulfuron and thifensulfuron, an increase in herbicide efficacy is observed when compared to X-77 (Chevron). The above adjuvant mixture was mixed at a 1% level with nicosulfuron, used at a rate of 1.5 gm ai/A and thifensulfuron, added at a 5:1 ratio rate with nicosulfuron. The mixture was applied to johnsongrass and giant foxtail (grown to the 3–4 leaf stage in a greenhouse) at a spray volume of 25 gal/A. The X-77 was mixed at a 0.5% level with the above herbicide mixture as well as with each herbicide alone. The results are shown in Table 9:

TABLE 9

| Treatment | Visual Injury 14 DAT | |
|---|---|---|
| | Johnsongrass | Giant Foxtail |
| Untreated Control | 0 | 0 |
| Nicolsulfuron + X-77 | 55 | 56 |
| Thifensulfuron + X-77 | 0 | 0 |
| Nicosulfuron/Thifensulfuron + | | |
| + X-77 | 51 | 58 |
| + Test Adjuvant | 84 | 86 |

EXAMPLE 10

When the test adjuvant is applied to seedling johnsongrass and giant foxtail with nicosulfuron an increase in herbicide efficacy is observed when compared to X-77 (Chevron). The above adjuvant mixture was mixed at a 1% level with nicosulfuron, used at a rate of 1.5 gm ai/A and applied to johnsongrass and giant foxtail (grown to the 3–4 leaf stage in a greenhouse) at a spray volume of 25 gal/A. The X-77 was mixed at a 0.5% level with the above herbicide. The results are shown in Table 10:

TABLE 10

| Treatment | Visual Injury (%) 14 DAT | |
|---|---|---|
| | Johnsongrass | Giant Foxtail |
| Untreated Control | 0 | 0 |
| Nicolsulfuron + X-77 | 58 | 58 |
| + Test Adjuvant | 89 | 89 |

EXAMPLE 11

When the test adjuvant is applied to seedling johnsongrass and giant foxtail with primisulfuron an increase in herbicide efficacy is observed when compared to the commonly used commercial product X-77 (Chevron). The above adjuvant mixture was mixed at a 1% level with primisulfuron, used at a rate of 0.8 gm ai/A (on Johnsongrass) and 6.0 gm ai/A (on giant foxtail), and applied at a spray volume of 25 gal/A. Both grass species were grown to the 3–4 leaf stage in a greenhouse. The X-77 was mixed at a 0.5% level with the above herbicide. The results are shown in Table 11:

TABLE 11

| Treatment | Visual Injury (%) 14 DAT | |
|---|---|---|
| | Johnsongrass | Giant Foxtail |
| Untreated Control | 0 | 0 |
| Primisulfuron + X-77 | 46 | 47 |
| + Test Adjuvant | 78 | 78 |

EXAMPLE 12

When the test adjuvant is applied to velvetleaf (*Abutilon theophrasti*) with acifluorfen an increase in herbicide efficacy is observed when compared to the commonly used Crop Oil Concentrate (COC). The above adjuvant mixture was mixed at a 1% level with acifluorfen, used at a rate of 59 gm ai/A and applied to velvetleaf grown to the 4 leaf stage in a greenhouse, at a spray volume of 25 gal/A. The COC was mixed at a 1.0% level with the above herbicide. The results are shown in Table 12:

TABLE 12

| Treatment | Visual Injury (%) to Velvetleaf 14 DAT |
|---|---|
| Untreated Control | 0 |
| Acifluorfen + COC | 56 |
| + Test Adjuvant | 82 |

EXAMPLE 13

When the test adjuvant is applied to velvetleaf with bentazon an increase in herbicide efficacy is observed when compared to the commonly used Crop Oil Concentrate. The above adjuvant mixture was tank mixed at a 1% level with bentazon, used at a rate of 254 gm ai/A and applied to velvetleaf (grown to the 4 leaf stage in a greenhouse) at a spray volume of 25 gal/A. The COC was mixed at a 1.0% level with the above herbicide. The results are shown in Table 13:

TABLE 13

| Treatment | Visual Injury (%) to Velvetleaf 14 DAT |
|---|---|
| Untreated Control | 0 |
| Bentazon + COC | 69 |
| + Test Adjuvant | 74 |

EXAMPLE 14

When the test adjuvant is applied to common lambsquarters (*Chenopodium album*) with thifensulfuron an increase in herbicide efficacy is observed when compared to the commonly used commercial product X-77 (Chevron). The above adjuvant mixture was tank mixed at a 1% level with thifensulfuron, used at a rate of 0.75 gm ai/A and applied to common lambsquarters at the 6 leaf stage, in a greenhouse at a spray volume of 25 gal/A. The X-77 was mixed at a 0.5% level with the above herbicide. The results are shown in Table 14:

TABLE 14

| Treatment | Visual Injury (%) to Common Lambsquarters 14 DAT |
|---|---|
| Untreated Control | 0 |
| Thifensulfuron + X-77 | 59 |
| + Test Adjuvant | 73 |

EXAMPLE 15

The adjuvant mixture described in Example 1 was tank mixed at a 1% level with thifensulfuron at a rate of 0.89 gm ai/A and 1.77 gm ai/A, and applied to plots of soybean for control of velvetleaf (*Abutilon theophrasti*), common lambsquarters (*Chenopodium album*), and pigweed (*Amaranthus* sp.), and compared to plots treated with the identical herbicide concentration and rate as above (without test adjuvant), but using a 0.125% inclusion rate of the nonionic surfactant (NIS) X-77. The plots were sprayed at a rate of 19.5 gal/A. The plots were analyzed for percent control by comparing the weed populations of the experimental plots to the untreated control. The results are shown in Table 15:

TABLE 15

| | Thifensulfuron Dose | | | | | |
|---|---|---|---|---|---|---|
| | 28.4 gm ai/A | | | 56.8 gm ai/A | | |
| | DAT | | | | | |
| Treatment | 8 | 17 | 28 | 8 | 17 | 28 |
| | Control Percentage | | | | | |
| Untreated Control | 0 | 0 | 0 | 0 | 0 | 0 |
| | Velvetleaf | | | | | |
| Test Adjuvant | 70 | 96 | 97 | 90 | 98 | 96 |
| NIS | 60 | 83 | 86 | 72 | 98 | 95 |
| | Common Lambsquarters | | | | | |
| Test Adjuvant | 88 | 92 | 95 | 90 | 94 | 95 |
| NIS | 68 | 80 | 89 | 85 | 91 | 97 |
| | Pigweed | | | | | |
| Test Adjuvant | 99 | 99 | — | 99 | 99 | — |
| NIS | 99 | 99 | — | 98 | 99 | — |

EXAMPLE 16

The adjuvant mixture described in Example 1 was tank mixed at a 1% level with primisulfuron at a rate of 16.2 gm ai/A, and applied to plots of field corn for control of annual grasses at a rate of 22 gal/A. These plots were compared to plots treated with the identical herbicide concentration and rate as above (without test adjuvant), but using a 1% inclusion rate of Crop Oil Concentrate (COC) and a 1% inclusion of COC plus a 4% inclusion of a 28% nitrogen solution (28% N). Prior to the test, the plots were treated with a pre-emergent soil application of dicamba (227 gm/A) to reduce interference from broadleaf weed pressure. The plots were analyzed for percent control by comparing the weed populations of the experimental plots to the untreated control. The results are shown in Table 16:

TABLE 16

| | Control Percentage DAT | |
|---|---|---|
| Treatment | 14 | 30 |
| Test Adjuvant | 79.3 | 71.0 |
| COC | 53.3 | 46.7 |
| COC + 28% N | 56.7 | 55.0 |
| Untreated Control | 0.0 | 0.0 |

EXAMPLE 17

The above adjuvant mixture was tank mixed at a 1% level with nicosulfuron, used at a rate of 6 gm ai/A and thifensulfuron, added at a 5:1 ratio rate with nicosulfuron, and applied to corn (Pioneer 3744) grown in a greenhouse at a spray volume of 25 gal/A. The results are shown in Table 17:

TABLE 17

| Treatment | Visual Injury (%) to Corn 14 DAT |
| --- | --- |
| Untreated Control | 0 |
| Nicosulfuron + X-77 | 5 |
| Thifensulfuron + X-77 | 0 |
| Nicosulfuron/Thifensulfuron | |
| + X-77 | 6 |
| + Test Adjuvant | 4 |

EXAMPLE 18

The above adjuvant mixture was tank mixed at a 1% level with primisulfuron, used at a rate of 6 gm ai/A and thifensulfuron, added at a 6:1 ratio rate with primisulfuron, and applied to corn (Pioneer 3744) grown in a greenhouse at a spray volume of 25 gal/A. The results are shown in Table 18:

TABLE 18

| Treatment | Visual Injury (%) to Corn 14 DAT |
| --- | --- |
| Untreated Control | 0 |
| Nicosulfuron + X-77 | 4 |
| Thifensulfuron + X-77 | 0 |
| Primisulfuron/Thifensulfuron | |
| + X-77 | 6 |
| + Test Adjuvant | 4 |

EXAMPLE 19

The adjuvant mixture of Example 1 that is tank mixed at a 1% level reduces the pH of alkaline water, as shown below in Table 19:

TABLE 19

| | pH | |
| --- | --- | --- |
| Water | 8.0 | 10.0 |
| Water + Adjuvant | 4.6 | 7.0 |

As shown in Example 19, the use of the inventive adjuvant reduces the pH of alkaline water used in mixing the spray solution. This is of importance when using herbicides, such as the sulfonyl ureas, which can be rapidly degraded when placed in an alkaline aqueous environment, thus losing their intended function.

While this invention has been described as having a preferred embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A herbicidal composition comprising as a major constituent a post-emergent herbicidally-active agent, said herbicidally-active agent comprising a sulfonyl urea herbicide, and including an effective amount of an adjuvant to increase the efficacy of said herbicidally-active agent, said adjuvant comprising acidulated soap stock derived from vegetable oil and a surfactant, wherein said surfactant is selected from the group consisting of alkylphenol ethoxylates, alkylbenzene sulfonates, alcohol ethoxylates, glycol ethers, ethoxylated sorbitan esters, polyethylene glycol esters, sorbitan esters, sulfosuccinates, phosphate esters, ethoxylated tallow amines and a blend of two or more of said surfactants, said acidulated soap stock comprising between about 50 wt % and 90 wt % of said adjuvant composition, and said surfactant comprising between about 10 wt % and 50 wt % of said adjuvant composition.

2. The composition of claim 1, wherein said adjuvant further includes mixed tocopherols as an additive, said added tocopherols comprising about 0.2–4.0 wt % of a mixture of said adjuvant and added tocopherols.

3. The composition of claim 1, wherein said herbicidally-active agent comprises at least one of nicosulfuron and primisulfuron.

4. The composition of claim 1, wherein said acidulated soap stock to surfactant ratio in said adjuvant is about 4:1, and wherein said adjuvant has sufficient ionic strength to lower the pH of said sulfonyl urea herbicide to a level sufficient to preserve said herbicide from degradation.

5. The composition of claim 1, wherein said adjuvant is present in said herbicidal composition in a concentration range of about 0.2% to 2.0%.

6. The composition of claim 5, wherein said adjuvant is present in said herbicide composition at a concentration range of about 1.0%.

7. A method for weeding of crops, comprising:
providing a herbicidal composition, said herbicidal composition comprising a sulfonyl urea herbicide and an effective amount of an adjuvant to increase the efficacy of the herbicide, said adjuvant comprising acidulated soap stock derived from vegetable oil and a surfactant, wherein said surfactant is selected from the group consisting of alkylphenol ethoxylates, alkylbenzene sulfonates, alcohol ethoxylates, glycol ethers, ethoxylated sorbitan esters, polyethylene glycol esters, sorbitan esters, sulfosuccinates, phosphate esters, ethoxylated tallow amines and a blend of two or more of said surfactants, said acidulated soap stock comprising between about 50 wt % and 90 wt % of said adjuvant composition, and said surfactant comprising between about 10 wt % and 50 wt % of said adjuvant composition; and applying to the weeds a herbicidally effective amount of the herbicide composition.

8. The method of claims 7, wherein said adjuvant further includes mixed tocopherols as an additive.

9. The method of claim 7, in which the surfactant is present in said composition in an acidulated soap stock to surfactant ratio of about 4:1; wherein the herbicide composition comprises a herbicide selected from the group consisting of primisulfuron and nicosulfuron; and wherein said adjuvant includes mixed tocopherols as an additive, said added mixed tocopherols comprising about 0.2–4.0 wt % of said adjuvant.

10. The method of claim 7, wherein said surfactant is a blend of alcohol ethoxylates and glycol ethers.

11. A method of combatting weeds comprising applying to said weeds or to a plot wherein weeds may occur a herbicidally effective amount of the composition of claim 1.

12. A herbicidal composition comprising the herbicide nicosulfuron, and an effective amount of an adjuvant to increase the efficacy of the herbicide, said adjuvant consisting essentially of a mixture of acidulated soap stock having a pH between 2 and 4, a surfactant and added mixed tocopherols; said acidulated soap stock being derived from soybean oil; said surfactant comprising at least one of alkylphenol ethoxylate, an alcohol ethoxylate and a glycol ether, and being present in said adjuvant in an acidulated soap stock to surfactant ratio of about 4:1; said added mixed tocopherols comprising about 0.2–4.0 wt % of said adjuvant.

13. The composition of claim 12, in which said acidulated soap stock includes C14 to C22 fatty acids, and wherein said adjuvant comprises about 1.0% of said herbicide composition.

14. The herbicidal composition of claim 12, wherein the pH of the acidulated soap stock is about 3.

* * * * *